United States Patent [19]

Kapralis et al.

[11] Patent Number: 4,559,047
[45] Date of Patent: Dec. 17, 1985

[54] HEAT PRODUCING MASK AND METHOD OF USE

[76] Inventors: Imants P. Kapralis, 3020 S. Punta Del Este Dr., Hacienda Heights, Calif. 91745; Harry Krukle, 7023 Bevis Ave., Van Nuys, Calif. 91405

[21] Appl. No.: 617,490

[22] Filed: Jun. 4, 1984

[51] Int. Cl.$^4$ .............................................. A61F 7/00
[52] U.S. Cl. .................... 604/291; 62/259.3; 128/399; 128/402; 128/403
[58] Field of Search ................... 128/399–403; 126/263, 204; 604/289–291; 62/259.3

[56] References Cited

U.S. PATENT DOCUMENTS

| 811,750 | 2/1906 | Speiske . | |
|---|---|---|---|
| 1,502,744 | 7/1924 | Perrault . | |
| 1,656,366 | 1/1928 | Sterling et al. . | |
| 1,679,432 | 8/1928 | Lyon . | |
| 1,894,775 | 1/1933 | Levenson . | |
| 2,157,169 | 5/1939 | Foster | 126/204 |
| 2,626,343 | 1/1953 | Fogel et al. | 128/380 |
| 2,827,438 | 3/1958 | Broadly | 252/70 |
| 3,093,308 | 5/1961 | Snelling | 236/1 |
| 3,175,558 | 3/1965 | Caillouette et al. | 128/403 |
| 3,223,081 | 12/1965 | Hunt | 126/360 |
| 3,463,161 | 8/1969 | Andrassy | 128/403 |
| 3,536,058 | 10/1970 | Hearst | 126/204 |
| 3,550,578 | 12/1970 | Fearon | 128/263 |
| 3,951,127 | 4/1976 | Watson et al. | 128/206 |
| 4,077,390 | 3/1978 | Stanley et al. | 126/263 |
| 4,379,448 | 4/1983 | Kapralis et al. | 126/263 |

FOREIGN PATENT DOCUMENTS 8200417  2/1982  PCT Int'l Appl. ................ 128/403

Primary Examiner—C. Fred Rosenbaum
Assistant Examiner—J. L. Kruter
Attorney, Agent, or Firm—William W. Haefliger

[57] ABSTRACT

A flexible mask includes a container for triggering of salt crystallization. The mask is manipulated to prevent stiffening, so as to be closely fitted to a human face to transmit heat thereto for therapeutic purposes.

31 Claims, 8 Drawing Figures

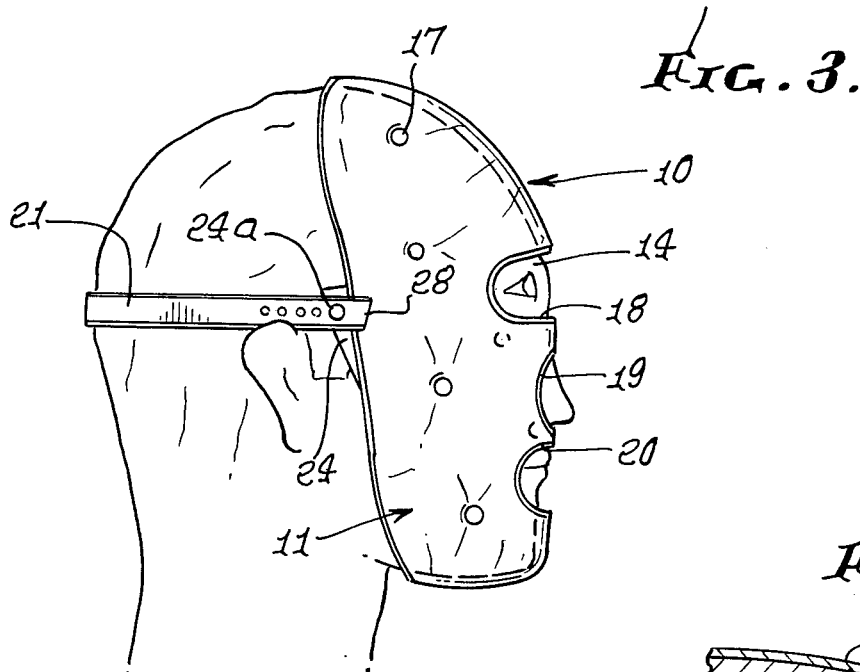
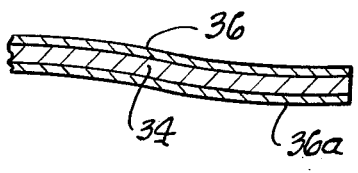
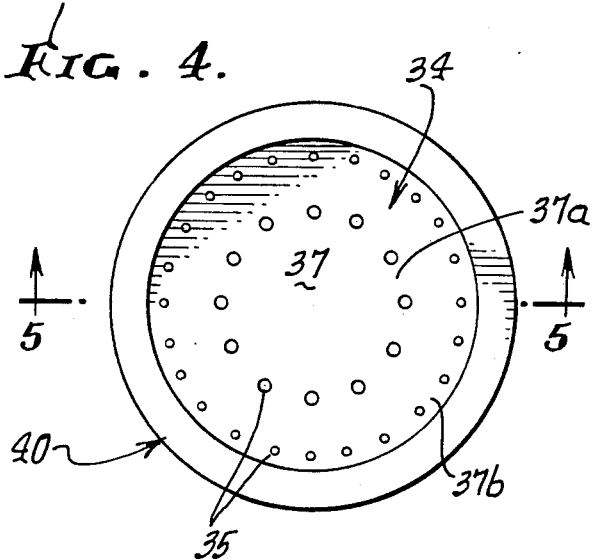
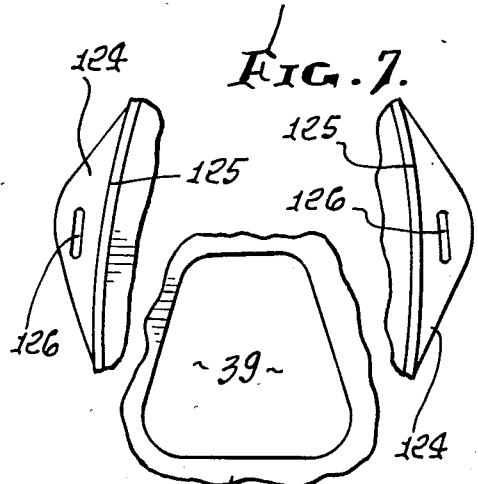
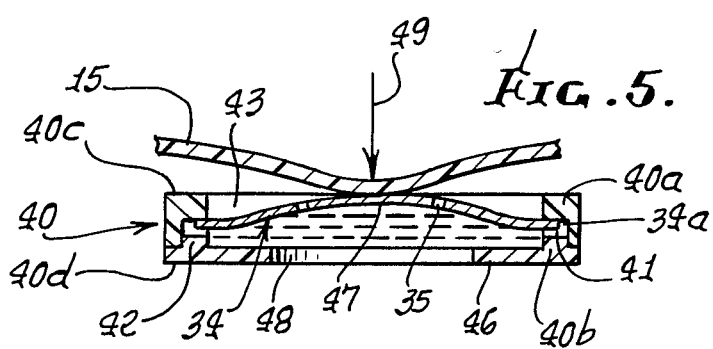

HEAT PRODUCING MASK AND METHOD OF USE

BACKGROUND OF THE INVENTION

This invention relates generally to heat packs, and more particularly to a face or body mask characterized as containing a supercooled salt solution that controllably crystallizes to produce heat.

Heat packs incorporating unusually advantageous trigger constructions are described in our U.S. patent application Ser. Nos. 177,258 and 565,699. There is need for a heat pack construction and method of use adapting it to face masks, and other body mask uses.

SUMMARY OF THE INVENTION

It is a major object of the invention to provide apparatus and method meeting the above need. Basically, and in its method aspects, the invention concerns the use of a heat producing mask to closely fit body contours and to transmit heat thereto, the mask including a flexible plastic container for a supercooled aqueous solution, and embodies the steps:

(a) triggering the crystallization of said solution to initiate exothermic heat production, (b) during said crystallization, preventing stiffening and maintaining flexibility, of said container and of the salt crystallizing therein, and (c) applying the warm flexible container to a contoured body to locally heat the body by heat conduction thereto.

As will appear, container stiffening is best prevented by massaging and repeatedly folding the container to displace salt crystals forming or just formed therein; heat may be concentrated and heat loss blocked by providing a flexible insulated sheet at one side of the container, the opposite side being applied to the facial contours; mask may be provided with a retainer strap to retain it to facial contours; and the beneficial effects of facial cream may be enhanced through use of the mask to produce concentrated heat application to skin pores. Further, the face mask containing the supercooled solution is amenable to chilling as in a refrigerator, so as to be applicable to facial contours for cold treatment, as immediately after heat application to the face using another mask in the manner described above.

In its apparatus aspects, the invention basically comprises:

(a) a flat plastic container having the form of a face mask, (b) said container containing a supercooled salt solution adapted for triggering of the solution to initiate crystallization accompanied by exothermic heat production, (c) said mask being flexible so as to be manually deformable during or immediately after said crystallization for preventing stiffening of the container and its contents, the mask sized for said close fitting to facial contours while flexible and warm, to heat the face.

As will appear, the opposite side walls of the container are preferably locally interconnected at spaced locations, to resist outward bulging and enhance mask local foldability or flexibility after salt crystallization; the mask may have through openings at eye, nose and mouth locations; and an improved triggering device may be employed in the salt solution, to float freely in the mask, as will be described.

These and other objects and advantages of the invention as well as the details of an illustrative embodiment, will be more fully understood from the following specification and drawings, in which:

DRAWING DESCRIPTION

FIG. 3 is a side elevation showing use of the mask;

FIG. 4 is a plan view of a trigger;

FIG. 5 is an enlarged section on lines 5—5 of FIG. 1;

FIG. 6 is a fragmentary view of a trigger in section, and

FIG. 7 is a modification.

DETAILED DESCRIPTION

Figure 1:
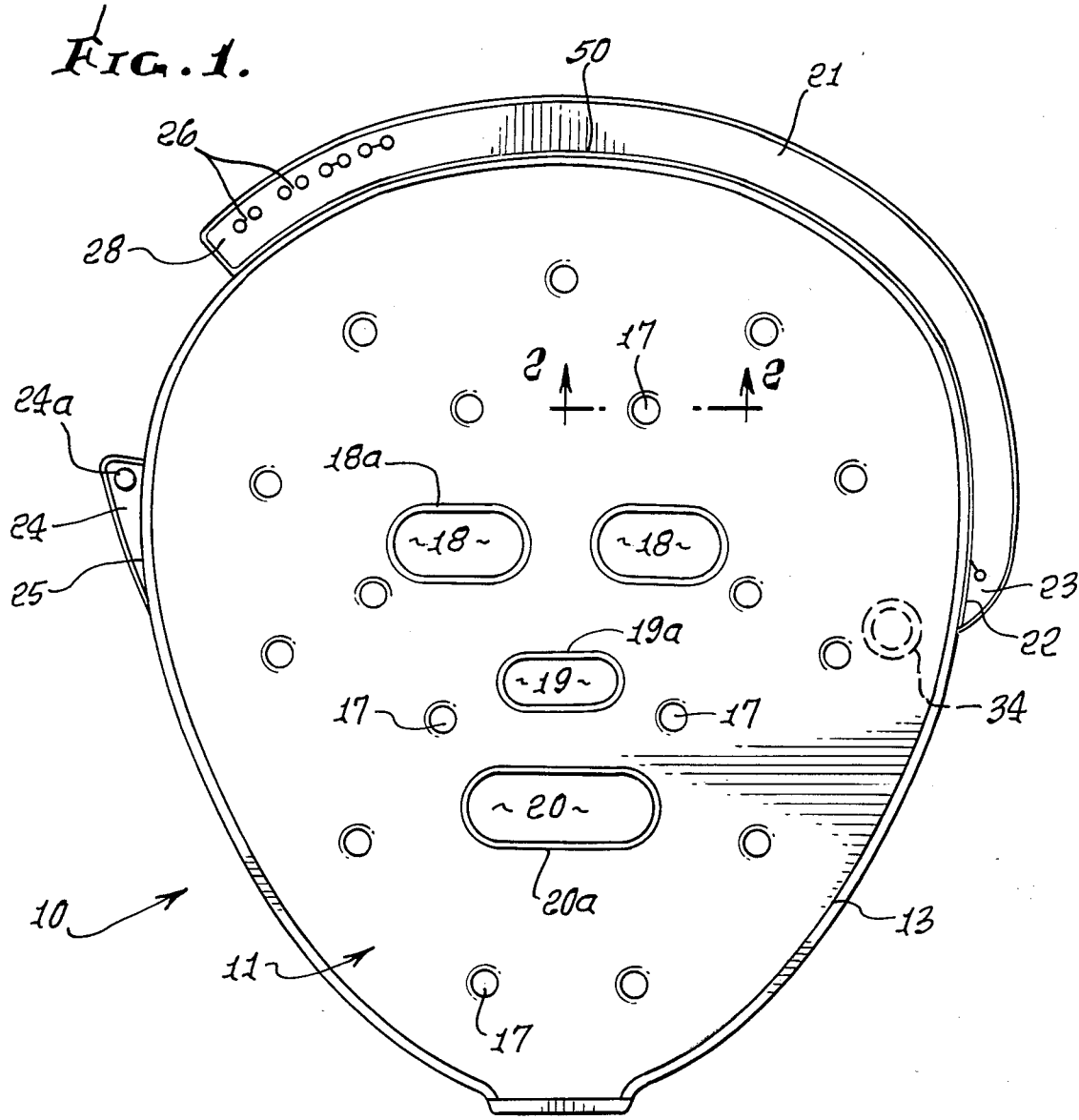
FIG. 1 is a plan view of a mask incorporating the invention.
Figure 2:
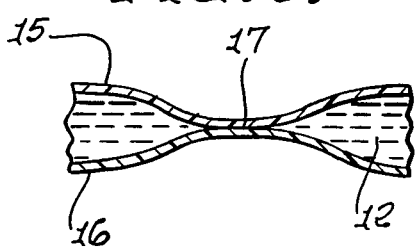
FIG. 2 is an enlarged section on lines 2—2 of FIG. 1.

Referring first to FIGS. 1 and 2, a flexible heat mask 10 includes a flexible plastic container 11 containing a supercooled solution 12, one example being aqueous sodium acetate as referred to in U.S. Pat. No. 4,077,390. The container may consist of translucent or transparent plastic, such as PVC, polyurethane and polyethylene coated polypropylene. The opposite walls 15 and 16 of the container may be peripherally bonded or heat sealed together as indicated at 13, whereby the solution 12 is contained against leakage.

The periphery of the flexible mask is oval-shaped as shown, and sized so that when applied to the face 14, as shown in FIG. 3, the mask will closely fit the facial contours, while warm, and despite crystallization of salt in the container tending to harden the container and its salt contents. Note that the container has opposite side walls 15 and 16 which are locally interconnected, as at heat sealed buttons 17 which are spaced apart over the flat container area. Such buttons resist outward bulging of the container walls by the pressure of solution 12, whereby liquid tends to remain in all positions of the container, and not to drain into the lowest portion thereof. The buttons also enhance mask conformability to facial contours in as much as they enhance container local foldability at their locations. Mask maximum thickness is normally less than ½ inch.

The container also has through openings at eye, ear or mouth locations 18–20, so as to register with these facial areas when applied to the human face 14, whereby close fitting to the face is further enabled. Note heat sealing of the container walls 15 and 16 about such openings, as at 18a, 19a and 20a.

An adjustable plastic retention strap 21 may be formed integrally with the container, so as to be boiled with the container to dissolve the salt in the supercooled solution during mask regeneration. One end of strap 21 is joined at 22 to one lateral edge portion 23 of the mask. The opposite end 28 of the strap is connectible to a plastic ear 24 integral with the opposite external edge portion 25 of the mask. Ear 24 may carry a plastic button 24a that interfits a selected slit 26 in a series of such slits formed in strap end 28, and the strap is thereby fitted around the wearer's head 29, as shown in FIG. 3. Strap may be cut free of the mask at line 50.

The method of use of the mask involves the steps:

(a) during said crystallization, preventing stiffening and maintaining flexibility, of said container and of the salt crystallizing therein, and (b) applying the warm flexible container to fit a contoured body to locally heat the body by heat conduction thereto.

In this regard, mask stiffening may be prevented by flexibly massaging or manipulating the mask during or immediately after salt crystallization. Triggering the latter may be carried out in many different ways, as for example by transmitting sideward pressure to the container, in the form of a sharp impact. A highly advantageous triggering device 34 may be located in the container and is described below.

Figure 2A:
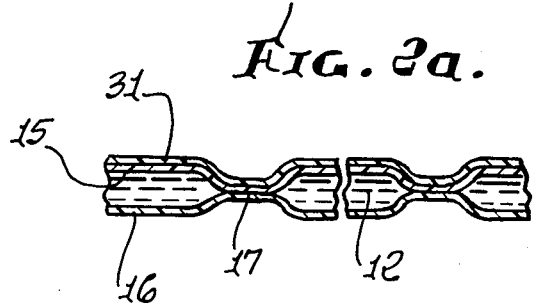
FIG. 2a is a view like FIG. 2.

FIG. 2a shows the use of a heat radiation blocking layer 31 on one side of the container, the opposite side of the container to be applied to the face. Thus, heat loss is reduced, and heat is concentrated for therapeutic transmission to the face, for longer periods. A therapeutic cream may be applied to the face prior to application of the hot mask, and a protective tissue may be interposed between the face and the mask. Also, a refrigerator chilled mask like the one described (before salt crystallization therein) may be applied over the face, after the warm mask is removed, for closing skin pores following opening of same induced by the hot mask. Layer 31 may consist of insulative plastic or fabric which is flexible.

TRIGGERING

Located in the container is a trigger 34 adapted to be deformed to initiate exothermic crystallization of the salt in the solution, and for that purpose the concentration of the salt is sufficient to produce such crystallization in response to trigger bending, as will be described. The trigger may be retained in the container at one location, or the trigger may freely float.

Generally speaking, the trigger comprises a thin strip, (for example about 0.005 inches thick) such as a non-ferrous metallic disc, having a perimeter indicated at 34a in FIG. 5. Workable non-ferrous metals have been found to include beryllium copper. Beryllium copper is a copper alloy containing a small amount of beryllium and typically some nickel or cobalt. The strip has a multiplicity of very small openings 35 formed therein, inwardly of perimeter 34a. Each opening or puncture is characterized as having opposed edges which face one another in near touching relation. Typically, the openings initially formed in the strip may be of pin-hole size. See U.S. patent application Ser. No. 177,258 filed Oct. 11, 1980.

The disc strip 34 is characterized as having two configurations between which it is bendable with snap-displacement causing the described edges to initiate progressive exothermic crystallization of the salt in the supercooled solution in the container. The user simply applies finger pressure on the container wall 15 and snap-deforms the disc 34, which causes the edges of the openings to actuate the crystallization, due to sudden deformation (as for example sudden local compression) of the solution trapped or confined in the spaces between the approximately touching edges. The snap-displacement of the nearly touching edges is found to initiate crystallization without failure or malfunction.

These purposes are served to unusual advantage by causing the disc to have dished configuration so as to "oil can" when deformed, i.e. easily snap over-center. Further the disc has a central portion 37 free of openings, and two outer annular sections 37a and 37b. The latter contain such openings, which are typically spaced inwardly from the perimeter 34a so that the latter is continuous, aiding the snap-displacement referred to.

The performance of the disc shaped strip to initiate crystallization is aided by impact orientation of the molecular structure as described in said U.S. patent application Ser. No. 177,258.

The disc or strip is typically protectively coated with a noble metal, such as gold, so as not to corrode or tarnish. See the coatings 36 and 37 on opposite surface of the disc 34, in FIG. 6. The coating for example has thickness less than 0.0001 inch, and may be electroplated on the strip or disc. Gold alloy (or silver) may also be used.

FIGS. 4 and 5 show the provision of a plastic (as for example DELRIN ) frame 40 about the perimeter 34a of the disc 34, to protect the disc. The ring-shaped frame includes two interconnected annular parts 40a and 40b, which loosely confine the perimeter 34a as in an annular groove 41 in the inner wall 42 of the frame, the disc edge free to move in that groove. The disc is sufficiently, or substantially completely confined within a zone 43 bounded by the frame, so that accidental triggering as by a moving surface acting on plastic container wall 15 is prevented. Zone 43 is located between planes and defined by frame annular surfaces 40c and 40d that face axially oppositely. Note also that the plastic frame prevents gouging or tearing of the plastic container by the peripheral edge of the metallic strip or disc. The edge may have shape other than circular, and the looping frame follows the shape of the strip edge. The frame allows liquid contact with all portions of the trigger.

The frame part 40b has a wall 46 opposite concave side 47 of the dished disc or strip, i.e. the strip bulges away from the wall 46. A central opening 48 in wall 46 allows fluid passage therethrough when the disc is depressed as indicated by arrow 49, and via plastic container wall 15. The disc is snap displaced relative to the frame 40.

Other form of triggering devices, or other triggering techniques, may be employed.

In FIG. 7, the modified nose and mouth openings are combined as one as indicated at 39, in mask 10'. Also, the plastic strap 21 is eliminated, and plastic ears 124 integral with opposite edges 125 of the mask have openings 126 to receive a suitable retainer band. The plastic container is indicated at 111, and otherwise has the same construction as in FIGS. 1 and 2.

We claim:
1. In the method of using a heat producing mask to closely fit body contours and transmit heat thereto, the mask including a flexible plastic container containing a supercooled aqueous salt solution, the steps that include:
   (a) providing a cup-shaped peripheral frame in the container for peripherally supporting a trigger strip so that the center portion of the trigger strip is free to flex relative to the frame, and triggering the crystallization of said solution to initiate exothermic heat production, by transmitting force via the container to the trigger strip and to said frame thereby to flex the trigger strip relative to the frame,
   (b) during said crystallization, preventing stiffening and maintaining flexibility, of said container and of the salt crystallizing therein, and

(c) applying the warm flexible container to a contoured body to locally heat the body by heat conduction thereto.

2. The method of claim 1 including removing said container from the contoured body, and applying a chilled mask, like the mask of claim 1, to the contoured body.

3. The method of claim 2 wherein said body comprises a human face, to which the masks are successively applied.

4. In the method of using a heat producing mask to closely fit body contours and transmit heat thereto, the mask including a flexible plastic container containing a supercooled aqueous salt solution, the steps that include
   (a) triggering the crystallization of said solution to initiate exothermic heat production,
   (b) during said crystallization, preventing stiffening and maintaining flexibility, of said container and of the salt crystallizing therein, and
   (c) applying the warm flexible container to a contoured body to locally heat the body to heat conduction thereto,
   (d) massaging the container to displace salt crystals to prevent stiffening and maintaining flexibility of the mask during re-crystallization.

5. The method of claim 4 wherein the container is substantially flat, with thickness less than about ½ inch, said triggering carried out by transmitting sideward pressure to the container.

6. The method of claim 4 wherein the container has walls and contains: a trigger to initiate salt crystallization when pressed, and a frame loosely peripherally supporting the trigger, and wherein said (a) step includes transmitting pressure to the trigger and frame via the container wall.

7. The method of claim 4 including providing flexible means at one side of said container that blocks heat radiation away from said side, the opposite side of said container being applied to said body contour.

8. In the method of using a heat producing mask to closely fit body contours and transmit heat thereto, the mask including a flexible plastic container containing a supercooled aqueous salt solution, the steps that include
   (a) triggering the crystallization of said solution to initiate exothermic heat production,
   (b) during said crystallization, preventing stiffening and maintaining flexibility, of said container and of the salt crystallizing therein, and
   (c) applying the warm flexible container to a contoured body to locally heat the body by heat conduction thereto,
   (d) said body comprising a human face, the container becoming substantially filled with crystallized salt, said (c) step including locally fitting the warm container and salt therein to the facial contours by locally exerting pressure against the container applied to the face.

9. The method of claim 8 wherein said container has the form of a face mask, with edge portions, and said local fitting of the container includes fitting said edge portions of the container to sides of the face and to the upper forehead.

10. The method of claim 8 including providing a retainer strap on the container, and adjustably fitting said strap around the rear of the human head.

11. The method of claim 8 including applying facial treatment liquid or cream to the face prior to said fitting of the container to the face to intimately heat said liquid or cream.

12. The method of claim 8 wherein the container has opposite walls which are locally interconnected at spaced locations to resist outward bulging of said walls, the container also having eye, nose and mouth openings, and said local fitting step includes registering said openings with the eyes, nose and mouth of human face.

13. A heat producing face mask to closely fit facial contours for transmitting heat thereto, comprising
   (a) a flat plastic container having the form of a face mask,
   (b) said container containing a supercooled salt solution adapted for triggering of the solution to initiate crystallization accompanied by exothermic heat production,
   (c) said mask being flexible so as to be manually deformable during or immediately after said crystallization for preventing stiffening of the container and its contents, the mask sized for said close fitting to facial contours while flexible and warm, to heat the face,
   (d) and including a trigger comprising a trigger strip in the container to which force is transmissible via a side wall to deform the trigger, thereby to initiate said crystallization, and a peripheral frame within the container loosely and peripherally supporting the trigger strip to allow the trigger strip to deform relative to the frame, the frame being free to move with the trigger in the container.

14. The mask of claim 13 wherein the container has opposite side walls, said side walls being locally interconnected at spaced locations to resist outward bulging of said side walls.

15. The mask of claim 14 having through openings at eye, nose and mouth locations.

16. The mask of claim 14 wherein the trigger is located to move about in the container and to be visible through a transparent wall of the container.

17. The mask of claim 14 including a heat radiation blocking layer on one side of the container.

18. The mask of claim 13 including an adjustable plastic retention strap integral with the container, with means for adjustably interfitting the strap to a human head.

19. The mask of claim 13 wherein said trigger strip comprises:
   (i) a thin, strip having a perimeter,
   (ii) said strip having a multiplicity of openings formed therein, each opening characterized as having opposed edges which face one another in near touching relation,
   (iii) the strip further characterized as having configurations between which it is bendable for causing said edges to initiate progressive exothermic crystallization of said salt in the solution.

20. The mask of claim 19 wherein said strip perimeter is generally circular, and said frame is generally annular.

21. The mask of claim 19 wherein said frame consists of molded plastic material loosely confining said perimeter.

22. The mask of claim 21 wherein said frame includes a wall extending at one side of the strip in closely spaced relation therewith, the frame also defining apertures at opposite sides of the strip, one aperture larger than the other.

23. The mask of claim 22 wherein said strip is metallic and has dished configuration in one of said configurations characterized as stable, and characterized in that the strip bulges away from said frame wall.

24. The trigger of claim 23 wherein said strip has a central portion and an outer portion surrounding said central portion, said openings located in one of said portions, the apertures being in registration with said central portion.

25. The trigger of claim 19 wherein said strip consists of beryllium copper.

26. The trigger of claim 19 including a noble metal coating on the strip.

27. The trigger of claim 26 wherein said noble metal consists essentailly of gold.

28. The trigger of claim 16 wherein the strip is in the form of a disc having two of said configurations between which the disc is bendable with snap displacement.

29. The trigger of claim 28 wherein said openings are distributed over the disc area, said openings having pin-hole size.

30. The mask of claim 13 wherein the trigger is free to float in the solution.

31. The mask of claim 13 including ears on the mask for retention of a retention strap that fits around the rear of the wearer's head.

* * * * *